(12) United States Patent  
Hendrickson et al.

(10) Patent No.: US 8,623,664 B2
(45) Date of Patent: Jan. 7, 2014

(54) URINE GENDER TEST KIT

(75) Inventors: Constance M. Hendrickson, Irving, TX (US); John Spurgeon, Whitesboro, TX (US)

(73) Assignee: Hello Baby, F.S.T., LLC, Whitesboro, TX (US)

( * ) Notice: Subject to any disclaimer, the term of this patent is extended or adjusted under 35 U.S.C. 154(b) by 768 days.

(21) Appl. No.: 12/428,652

(22) Filed: Apr. 23, 2009

(65) Prior Publication Data

US 2009/0233376 A1 Sep. 17, 2009

Related U.S. Application Data

(63) Continuation-in-part of application No. 11/219,985, filed on Sep. 6, 2005.

(60) Provisional application No. 60/612,411, filed on Sep. 23, 2004.

(51) Int. Cl.
*G01N 33/00* (2006.01)

(52) U.S. Cl.
USPC .......................................... 436/166; 436/172

(58) Field of Classification Search
USPC .................... 436/166, 172; 422/61, 68.1
See application file for complete search history.

(56) References Cited

U.S. PATENT DOCUMENTS

| | | |
|---|---|---|
| 4,840,914 A | 6/1989 | Weisberg |
| 5,709,837 A | 1/1998 | Mori et al. |
| 6,420,182 B1 | 7/2002 | Start |
| 2006/0063270 A1 | 3/2006 | Spurgeon et al. |

OTHER PUBLICATIONS

Ostler, et al.; "Fetal sex determination; the predictive value of 3 common myths"; JAMC, Dec. 14, 1999; pp. 1525-1526.

*Primary Examiner* — Sam P Siefke
(74) *Attorney, Agent, or Firm* — Edwin S. Flores; Chainey P. Singleton

(57) ABSTRACT

A kit for determining the gender of an unborn fetus. The kit comprises a container holding a solid composition therein, the solid composition including a basic salt and a transition metal. An atmosphere in the container is substantially free of water.

20 Claims, 5 Drawing Sheets

URINE GENDER TEST KIT

CROSS-REFERENCE TO RELATED APPLICATIONS

This application is a continuation-in-part application of U.S. patent application Ser. No. 11/219,985, filed Sep. 6, 2005 entitled, "URINE GENDER TEST," to John Spurgeon and Constance M. Hendrickson, which in turn, claims the benefit of U.S. Provisional Application 60/612,411 of the same title, filed on Sep. 23, 2004, and which are incorporated by reference herein in their entirety.

TECHNICAL FIELD OF THE INVENTION

The present invention is directed, in general, to determining the gender of an unborn fetus by testing the urine from a pregnant mother, and more particularly, a composition, method and kit to facilitate such testing.

BACKGROUND OF THE INVENTION

There is great interest in determining the gender of an unborn fetus. For instances, parents are curious to know the sex of their unborn child. Knowledge of a fetus's gender would allow animal breeders to better manage various aspects of their business, including selling and purchase, insurance, mating decisions. Unfortunately, an accurate gender test that is both inexpensive and simple to perform is not available.

Various tests, such as the Draino test, while inexpensive and simple to perform, has been dismissed by the medical establishment as having no value for predicting fetal sex. Other techniques that are accepted as accurate, are either invasive, such as amniocentesis or maternal blood tests, or require expensive equipment, such as ultrasound or x-rays. Moreover, such techniques are not without dangers to the fetus and are not completely reliable.

Accordingly, what is needed in the art is a gender test that does not suffer from the disadvantages associated with conventional gender tests, as discussed above.

SUMMARY OF THE INVENTION

To address the above-discussed deficiencies of the prior art, the present invention provides in one embodiment, a kit for determining the gender of an unborn fetus. The kit comprises a container holding a solid composition therein, the solid composition including a basic salt and a transition metal. An atmosphere in the container is substantially free of water.

Another embodiment is a method of manufacture the kit. The method comprises forming a solid composition in a container, including placing a transition metal in a container and placing a basic salt in the container. The method also comprises flushing the container with an atmosphere that is substantially free of water.

Still another embodiment is a method of determining the gender of an unborn fetus. The method comprises adding urine from a pregnant female to a container holding the above-described solid composition and atmosphere substantially free of water. The method also comprises mixing the solid composition and the urine to form a solution, and, comparing a color of the solution to a color standard to determine a gender of an unborn fetus carried by the female.

The foregoing has outlined preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the scope of the invention.

BRIEF DESCRIPTION OF THE DRAWINGS

For a more complete understanding of the present invention, reference is now made to the following detailed description taken in conjunction with the accompanying FIGUREs. It is emphasized that various features may not be drawn to scale. In fact, the dimensions of various features may be arbitrarily increased or reduced for clarity of discussion. Reference is now made to the following descriptions taken in conjunction with the accompanying drawings, in which.

DETAILED DESCRIPTION

Figure 1:
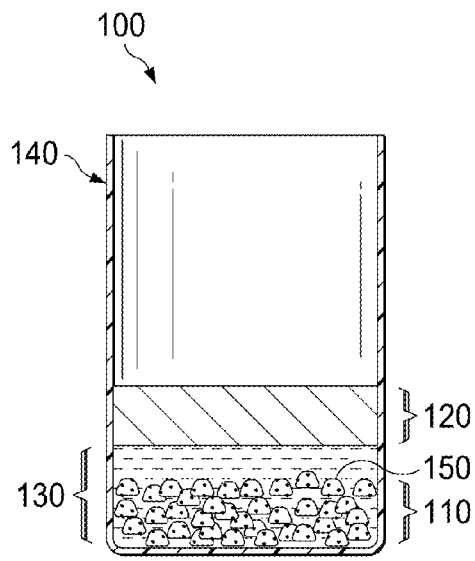
FIG. 1 illustrates a cross-sectional view of an exemplary solid composition of the present invention for gender testing.

One embodiment of the present invention is a solid composition for determining the gender of an unborn fetus. The term fetus, as used herein is defined as the unborn offspring of any animal species, such as human, bovine and equine species. FIG. 1 illustrates a cross-sectional view of an exemplary solid composition 100 of the present invention. The present invention benefits from the recognition that the shelf-life of the solid composition 100 can be advantageously extended by keeping certain components of the solid composition 100 separated, to prevent the undesired premature reaction of these components.

As illustrated in FIG. 1, the solid composition 100 comprises a first layer 110, a second layer 120 and a third layer 130. The third layer 130 separates the first layer 110 from the second layer 120. The first layer 110 comprises a basic salt. As well known to those of ordinary skill in the art, a basic salt is defined as a salt that contains more of the basic constituent than is required to neutralize the acid of the salt. In some preferred embodiments, the basic salt of the first layer 100 comprises a water-soluble alkali metal hydroxide. In some embodiments, the basic salt comprises lithium hydroxide (LiOH), sodium hydroxide (NaOH), potassium hydroxide (KOH) or a mixture thereof. In some cases, the basic salt preferably comprises a non-deliquescent basic salt, such as LiOH, because such salts are less prone to absorb water and carbon dioxide from air and thereby do not liquefy during storage as rapidly as deliquescent basic salts such as KOH or NaOH. The liquefaction of the first layer 110 can cause the undesirable premature mixing and reaction of the components of the first and second layers 110, 120. In some cases, the basic salt preferably comprises NaOH or KOH, because these salts generate a large amount of heat when it dissolves in water or urine. The generation of heat, in turn, facilitates other components to dissolve when the solid composition 100 is mixed with urine for gender testing.

In some advantageous embodiments, such as that shown in FIG. 1, the first layer 110, comprising a basic salt is a top layer of the solid composition 100 located in a container 140. In other preferred embodiments, however, the first layer 110 can be a bottom layer of the composition 100. Preferably, the first layer 110 comprises solid particles of the basic salt whose size is carefully selected. The selection balances the desire for the particle size to be small enough to rapidly dissolve in an aqueous solution, versus having a large enough size to retain the separation of the first and second layer 110, 120 via the third layer 130. In some instances, the first layer 110 comprises pellets or flakes having an average diameter ranging from about 1 millimeter to 10 millimeters. In some preferred embodiments, the first layer 110 comprises about 5 to about 25 percent of the total weight of the solid composition 100.

The second layer 120 comprises a transition metal. For the purposes of the present invention, a transition metal is defined as any element in Periods 4-6 and Groups 3-12 of the Periodic Table of Elements (International Union of Pure and Applied Chemist Convention for designating Groups and Periods). In some preferred embodiments, the transition metal, upon being dissolved in an aqueous solution, forms ions having a valance of +2 or +3. In some embodiments of the solid composition 100, the transition metal comprises aluminum, iron or a mixture thereof. In certain preferred embodiments, the transition metal comprises aluminum because aluminum is less prone to oxidation than iron when the solid composition 100 is stored over a period of 3 to 4 months. In addition, the solid composition 100 comprising aluminum provides a more readily recognizable color difference between positive and negative results in gender tests, as compared to an iron-containing solid composition 100.

In certain preferred embodiments, such as shown in FIG. 1, the second layer 120 is a bottom layer of the solid composition 100 in the container 140. In other preferred embodiments, however, the second layer 120 can be the top layer of the solid composition 100. Preferably, the second layer 120 comprises solid particles 150 of the transition metal whose size and amount is carefully selected. The selected size and amount of transition metal balances the desire for the particle size to be small enough to rapidly dissolve and react with the basic salt and urine sample but not to have an excessively violent reaction. An excessively violent reaction might result in the frothing of the solid composition 100 or the urine sample out of the container 140 or cause the container 140 to explode.

In some instances, the second layer 120 advantageously comprises particles 150, such as shot or filings, having an average diameter ranging from about 1 millimeter to 2 millimeters. In some preferred embodiments, the second layer 110 comprises about 4 to about 20 percent, and more preferably about 4 to about 12 percent, of the total weight of the solid composition 100.

The third layer 130 comprises a neutral filler. The neutral filler can comprise a neutral salt, a water soluable polymer, or both, and is configured to separate the first and second layers 110, 120. Keeping the basic salt of the first layer 110 and transition metal of the second layer 120 separated advantageously extends the shelf life of the solid composition 100. The shelf life is extended by deterring oxidation and other reactions between the basic salt and the transition metal of the first and second layers, 110, 120, respectively. For example, embodiments of the solid composition 100 of the present invention can be kept for periods of up to about 4 months and then successfully used for gender testing. This is in contrast to formulations comprising a basic salt and a transition metal in intimate contact with each other. In such formulations, the basic salt and transition metal start reacting with each other within minutes of their preparation.

As well known to those of ordinary skill in the art, a neutral salt is formed by the complete replacement of the hydrogen in an acid or base, in the former case by a positive or basic element or radical, in the latter case by a negative or acidic element or radical. Preferred embodiments of the neutral salt comprises a water soluable salt such as alkali halides, sulfates or nitrates. Preferred embodiments of the neutral filler comprising the water soluable polymer include polyvinyl alcohol, polyvinyl alcohol or a mixture thereof.

In certain advantageous embodiments, such as shown in FIG. 1, the third layer 130 is located between the first and second layers 110, 120. More preferably, as also shown in FIG. 1, the third layer 130 encapsulates the particles of second layer 120. In other preferred embodiments, however, the third layer 130 can encapsulate the basic salt of the first layer 110. In some preferred embodiments, the third layer 130 comprises about 30 to about 80 percent, and more preferably about 55 to about 80 percent, of the total weight of the solid composition 100.

In still other preferred embodiments the solid composition 100 further includes an indicator. The indicator advantageously facilitates a more prominent color change in the solution resulting from mixing the solid composition 100 with testosterone-containing urine as compared to testosterone-free urine during gender testing. The indicator can comprise any acid-base indicator that preferably turns pink or red with high pH. In some preferred embodiments, the indicator comprises alizarin, alizarin yellow R, o-cresolphthalein, cresol red, phenol red, phenolphalien, or mixtures thereof. In certain advantageous cases, such as shown in FIG. 1, the third layer 130 includes the indicator. In other cases, not illustrated, the first layer includes the indicator, and in still other instances, both the first and third layer includes the indicator. In some preferred embodiments, the indicator comprises about 0.1 to about 0.3 percent of the total weight of the solid composition 100.

Another aspect of the present invention is a method for preparing a solid composition for determining the gender of an unborn fetus. FIGS. 2 to 5 illustrate cross-sectional views of selected steps in an exemplary method of preparing a solid composition 200 according to the principles of the present invention. Any embodiments of the solid composition, and its the components discussed above and illustrated in FIG. 1, can be made according to the method.

Figure 2:
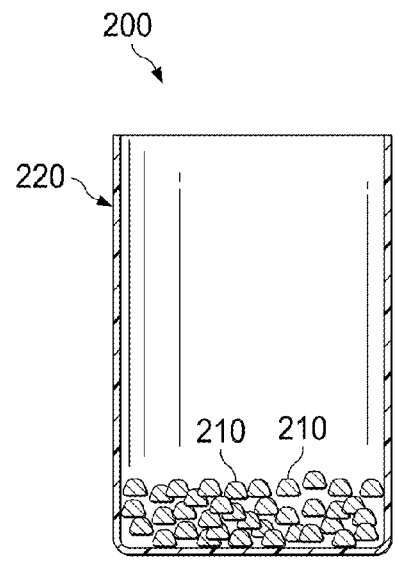
FIGS. 2-6 illustrate cross-sectional views of selected steps in an exemplary method of manufacturing a solid composition for gender testing according to the principles of the present invention.

Turning first to FIG. 2, illustrated is the partially completed solid composition 200, after a placing a transition metal 210 in a container 220.

Figure 3:
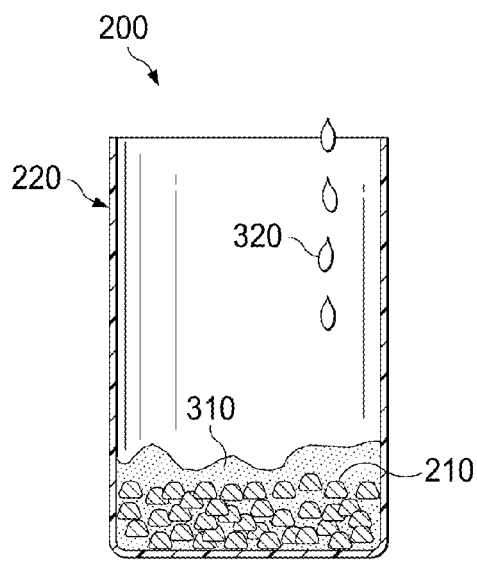
Figure 4:
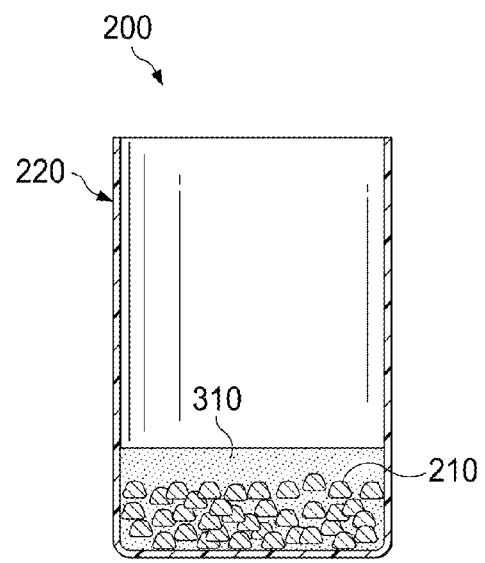

FIGS. 3 and 4 illustrate placing a neutral filler 310 in the container 220. In the illustrated embodiment, the filler 310 covers the transition metal 210. More preferably, the filler 310 encapsulates the transition metal 210. Turning first to FIG. 3, to facilitate encapsulation of the transition metal 210 by the neutral filler 310, a liquid 320 is added to wash the transition metal 210 and the neutral filler 310 to the bottom of the container 220.

In some cases, the neutral filler 310 comprises a neutral salt dissolved in the liquid 320 to form a solution, and the solution is placed in the container 220. In some instances, the liquid 320 comprises water, a volatile organic solvent such as acetone or ethanol, or a mixture thereof. In still other cases, the neutral salt 310, the liquid 320, or both, or a solution thereof, are placed in the container 220, and then the transition metal 210 is added to the container 220. In other embodiments, the neutral filler 310 comprises a water soluable organic polymer.

With continuing reference to FIG. 3, FIG. 4 shows the partially completed solid composition 200 after drying to leave the transition metal 210 encapsulated and covered by the neutral filler 310. Drying can be accomplished by heating to slightly below the boiling point of the liquid 320 (e.g., about 94° C. when the liquid is water). Alternatively, drying can be achieved in vacuum at room temperature (about 20° C.) or at lower than room temperatures, via freeze-drying. In some cases, as illustrated in FIG. 4, drying removes the liquid 320 thereby allowing the neutral salt of the neutral filler 310 to precipitate and crystallize around the transition metal 210. In other cases, drying condenses the water soluble organic polymer of the neutral filler 310, so that the organic polymer surrounds the transition metal 210.

Figure 5:
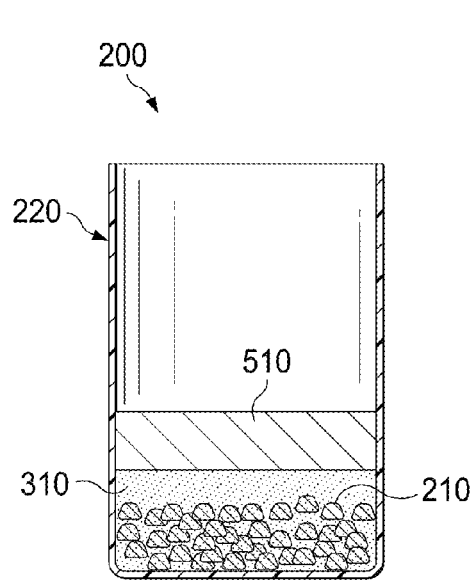

Turning now to FIG. 5, illustrated is the partially completed solid composition 200, after adding a basic salt 510 to the container 220. In some preferred embodiments, as illustrated in FIG. 5, the basic salt 510 is placed over the neutral filler 310. The neutral filler 310 thereby separates the transition metal 210 and the basic salt 510.

Though not illustrated, in other embodiments of the method, an optional indicator such as described above, is added to one or both of the neutral filler 310 or the basic salt 510. In alternative embodiments of the method, the basic salt 510 is placed in the container first, followed by adding the neutral filler 310, to cover the basic salt, and then adding the transition metal 210. In yet other cases, the neutral filler 310 and basic salt 510, and optional indicator, are mixed together, and then moistened with a liquid 320 to facilitate their placement in the bottom of the container 220, followed by drying, and then the transition metal 210 is placed over the neutral filler 310.

Figure 6:
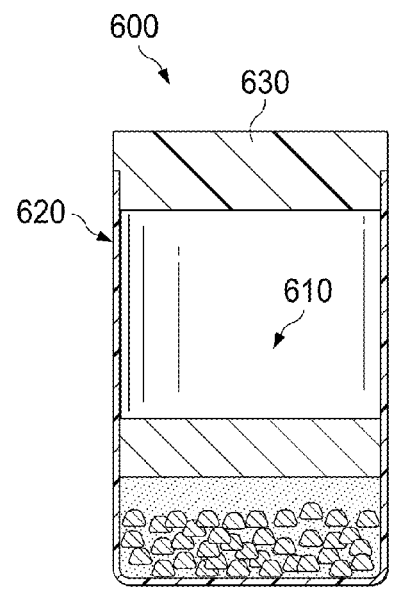

Yet another aspect of the present invention is a kit for determining the gender of an unborn fetus. FIG. 6 illustrates a cross-sectional view of an exemplary kit 600 of the present invention. The kit 600 comprises a solid composition 610 located in a reaction vessel 620. Any of the embodiments of the solid composition discussed above and illustrated in FIGS. 1-5 can be included in the kit 600. Some preferred embodiments of the reaction vessel 620 comprise a non-metallic material, and more preferably, the reaction vessel 620 is substantially non-reactive with the components of the solid composition 610. Preferred embodiments of the reaction vessel 620 comprise glass or plastic tubes or vials.

The solid composition 600 is separated from the ambient environment surrounding the reaction vessel 620 by a seal 630 covering an opening in the reaction vessel 620. The seal 630 advantageously deters the uptake of moisture from the ambient environment into the solid composition 610. If it absorbs sufficient quantities of moisture, components of the solid composition 610 can get mixed together and react as discussed above, thereby spoiling the kit 600.

In some preferred embodiments, the seal 630 comprises a wax that forms an airtight closure over an opening in the reaction vessel. Preferred waxes comprise a petroleum wax such as paraffin wax, although other animal, plant or synthetic waxes can be used. In other embodiments, however, the seal comprises a plastic screw top cap or similar airtight closure. Alternatively, the top of the reaction vessel 620 can be sealed by melting the upper portion of the reaction vessel 620 together.

Forming an airtight seal 630 over the reaction vessel 620 advantageously extends the shelf life of the kit 600. For example, in some embodiments of the kit 600 having a seal 630 made of paraffin wax, the kit 600 can be stored for least about 2 years before being successfully used. In comparison, similarly formulated solid compositions 610 placed in unsealed reaction vessels 620 have a shelf-life up to about 4 months.

Figure 7:
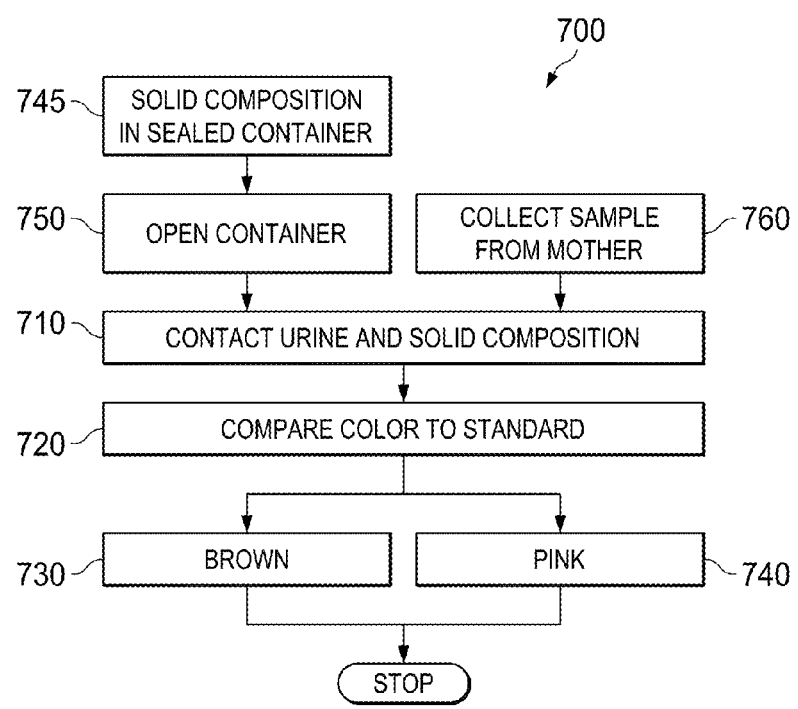
FIG. 7 illustrates by flow diagram, an exemplary method of determining the gender of an unborn fetus according to the principles of the present invention.

Still another aspect of the present invention is a method of determining the gender of an unborn fetus. FIG. 7 illustrates by flow diagram an exemplary method 700 of determining the gender of an unborn fetus according to the principles of the present invention. The method 700 comprises in step 710, contacting urine from a mother of the unborn fetus with a solid composition of the present invention to form a solution. Any of the embodiments of the solid composition and its packaging discussed herein can be used in the method 700. The method 700 further includes in step 720, comparing a color of the solution to a color standard to determine a gender of the unborn fetus.

FIG. 7, further illustrates aspects of the color comparison. In step 730, the solution turns dark brown when the urine is from a mother pregnant with a male fetus. As illustrated in step 740, in some preferred embodiments, when the urine from a mother pregnant with a female fetus is added to the solid composition that includes an indicator, the resulting solution turns pink or red.

As exemplified in step 745, in some preferred embodiments, the solid composition is stored in a sealed container. Then, as shown in step 750, shortly before testing, the seal of the container is opened so that urine from the mother can be added to the container. In some preferred embodiments, the seal is opened within about 1 hour of adding urine to the container. As further exemplified by step 760, the urine sample is preferably obtained from the mother within about 1 hour before adding the urine to the container holding the solid composition.

Aspects of present invention are illustrated in the following examples. It will be appreciated that the examples are presented solely for the purpose of illustration and should not be construed as limiting the invention. For instance, although the studies described below may be carried out in a laboratory setting, one skilled in the art could adjust specific numbers, dimensions and quantities up to appropriate values for a full-scale plant setting.

EXAMPLES

Exemplary data collected as part of the present invention is depicted below to: 1) illustrate the preparation of various solid compositions of the present invention; 2) demonstrate the superior stability of the solid composition of the present invention as compared a prior art formulations; 3) present test results to demonstrate the determination of gender in humans using test kits of the present invention; and 4) present test results to illustrate the feasibility of determining gender in bovine and equine species.

Various solid compositions were prepared and subject to stability testing and to investigate gender testing. One solid composition (designated SC-1) comprised a transition metal of iron powder, a neutral filler of KCl, and a basic salt of KOH, in weight percentages of 10%, 65%, and 25%, respectively. A second solid composition (designated SC-2) comprised a transition metal of aluminum powder, a neutral filler of sodium nitrate ($NaNO_3$) and a basic salt of NaOH in weight percentages of 5%, 75%, and 20%, respectively. A third solid composition (designated SC-3) comprised a transition metal of aluminum shot (average diameter of between about 1 and 2 mm), a neutral filler of NaCl and $NaNO_3$, and a basic salt of NaOH in weight percentages of 6%, 20%, 60%, and 14%, respectively. A fourth solid composition (designated SC-4) comprised a transition metal of iron filings, a neutral filler of potassium chloride (KCl) and potassium nitrate ($KNO_3$) and a basic salt of NaOH in weight percentages of 12%, 25%, 55%, and 6%, respectively.

In one study, a solid composition (designated SC-5) used for stability testing was composed of the same transition metal, neutral filler and basic salt, and substantially the same proportions thereof, as SC-3. The aluminum shot was added to a glass test tube and then a neutral filler comprising NaCl and $NaNO_3$ (about 1:3 weight ratio) was added to the test tube. In addition, an indicator of about 0.1 weight percent phenolphthalein was added to the test tube. Next, several drops of water were added to the tube to wet the neutral filler, indicator and aluminum shot. The test tube was then gently tapped to ensure that all of the aluminum shot was at the bottom of the test tube and covered by the wet neutral filler. The tube was then heated to about 94° C. to evaporate the water. As the water evaporated, the neutral filler crystallized, thereby encapsulating the transition metal underneath the neutral filler. After cooling the tube, the NaOH pellets were added to the tube over the neutral filler. In some preparations, the tube was then sealed with paraffin wax until used for testing, while in other preparations the tube was left exposed to the ambient environment (about 50 to 85 percent relative humidity).

Figure 8A:
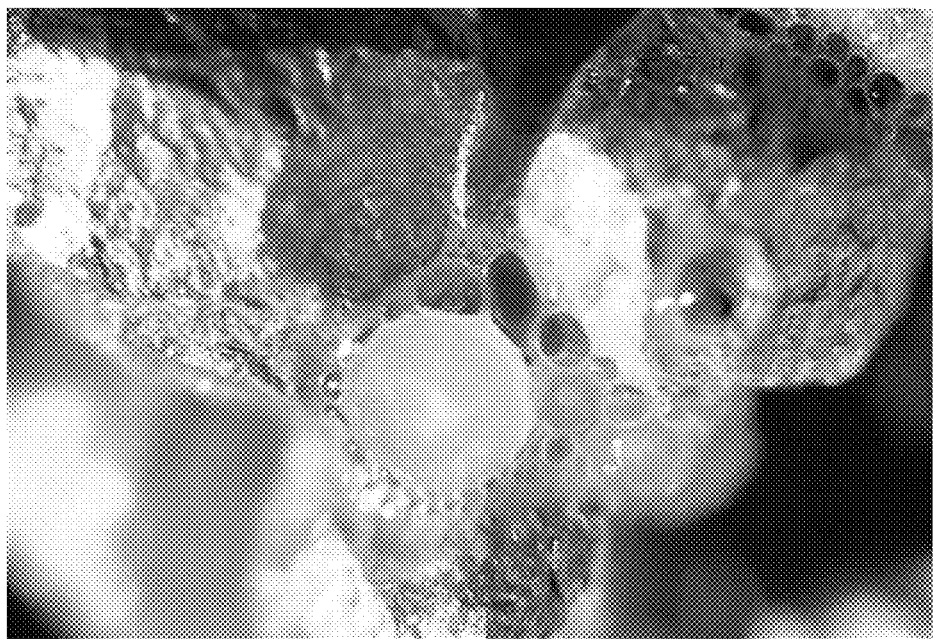
FIGS. 8A and 8B present representative microphotographs of a typical prior art composition, at two different magnifications, minutes after mixing components of the composition.
Figure 8B:
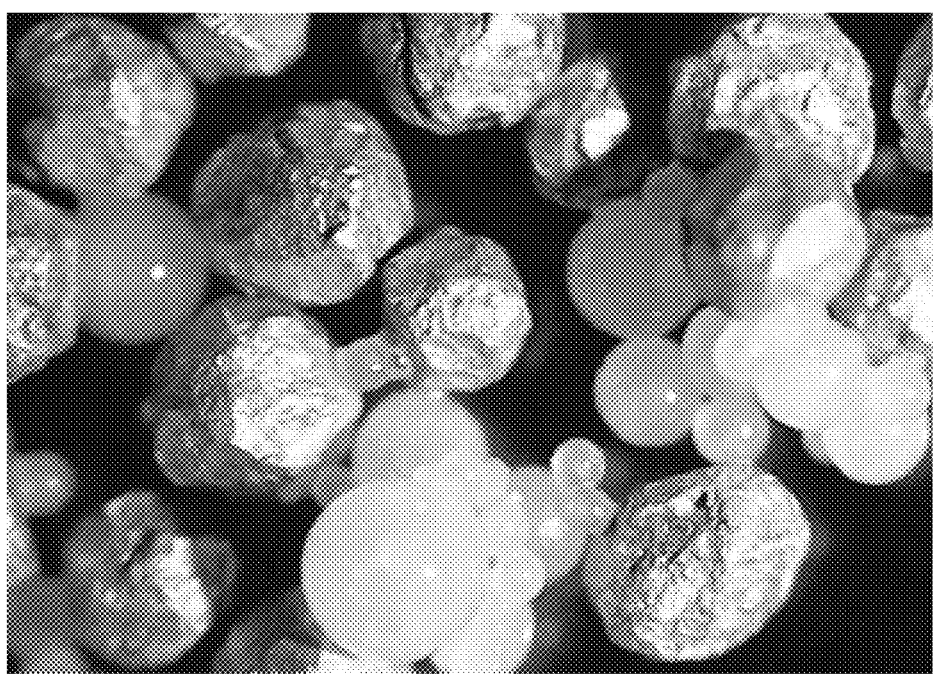

For comparative purposes, a test formulation (designated F-1) was prepared by mixing the aluminum shot with NaOH in proportions of 50:50 (wt/wt), with no neutral filler present in the formulation. Preparation F-1 is representative of prior art formulation where aluminum and alkali hydroxide are in intimate contact with each other. FIGS. 8A and 8B presents representative microphotographs, at two different magnifications, of the F-1 preparation minutes (e.g., less than 10 minutes) after mixing the aluminum shot and NaOH together. Substantial oxidation reactions between the aluminum shot and NaOH were observed, the reaction continuing until either all the aluminum or the NaOH was consumed. Similar experiments where similar proportions of aluminum powder and NaOH were mixed directly together resulted in a violent reaction, and in some cases, explosion of the reaction vessel.

Additional experiments were performed to evaluate the long-term stability of the SC-5 preparation. Several test tubes containing the SC-5 preparation were stored in unsealed test tubes. These preparations worked accurately for gender testing for up to about 3.5 months. Thereafter, the accumulation of moisture in the test tubes became visible. The content of all of the tubes had undergone substantial reactions after about 4.25 months. Dramatically longer stabilities were observed for several test tubes containing SC-5 preparations in sealed test tubes. Preparations of SC-5 stored in sealed tubes have been accurately used for gender test after about 24 months of storage. Similar stabilities have been obtained for preparations stored in containers with damp tight packages.

Representative results for gender test performed using the SC-5 preparation on human subject are shown in Table 1. Similar test results for equine and bovine subjects are shown in TABLE 2.

TABLE 1

| Sample Number | Mother's Age (Years) | Gestational Age at Testing (Weeks) | Test Result | Confirmed Result |
| --- | --- | --- | --- | --- |
| 1 | 19 | 16.5 WKS | F | F |
| 2 | 38 | 26 WKS | F | F |
| 3 | 15 | 19 WKS | M | M |
| 4 | 20 | 17 WKS | F | F |
| 5 TWINS DIFFERENT GENDER | 19 | 16 WKS | M | F |
| 6 | 21 | 21 WKS | F | F |
| 7 TWINS DIFFERENT GENDER | 31 | 18 WKS | F | M |
| 8 | 36 | 18 WKS | F | F |
| 9 | 18 | 19 WKS | F | F |
| 10 | 23 | 17 WKS | M | M |
| 11 | 28 | 19 WKS | M | M |
| 12 | 22 | 20 WKS | F | F |
| 13 | 23 | 21 WKS | F | F |
| 14 | 21 | 20 WKS | F | F |
| 15 | 19 | 22 WKS | M | M |
| 16 | 26 | 16 WKS | M | M |
| 17 | 25 | 15.5 WKS | F | F |
| 18 | 22 | 18 WKS | F | F |
| 19 | 31 | 19.5 WKS | F | F |
| 20 EVENING URINE | 18 | 16 WKS | F | M |
| 21 | 19 | 17 WKS | M | M |
| 22 | 20 | 21 WKS | F | F |
| 23 | 20 | 20 WKS | F | F |
| 24 | 26 | 22 WKS | F | F |
| 24 | 20 | 20 WKS | F | F |
| 25 | 22 | 21 WKS | M | M |
| 26 | 22 | 16 WKS | F | F |
| 27 | 24 | 18 WKS | M | M |
| 28 | 24 | 19 WKS | M | M |
| 29 | 34 | 19 WKS | M | M |
| 30 TO EARLY IN GEST | 39 | 14 WKS | F | M |
| 31 | 26 | 21 WKS | F | F |
| 32 | 28 | 20 WKS | F | F |
| 33 | 29 | 20 WKS | F | F |
| 34 | 31 | 22 WKS | F | F |
| 35 | 36 | 21 WKS | F | F |
| 36 | 27 | 17 WKS | F | F |
| 37 | 29 | 17 WKS | F | F |
| 38 | 24 | 19 WKS | F | F |
| 39 | 22 | 17 WKS | M | M |
| 40 | 26 | 17 WKS | M | M |
| 41 | 19 | 22.5 WKS | M | M |
| 42 | 21 | 21 WKS | F | F |
| 43 | 27 | 16 WKS | M | M |
| 44 | 25 | 17 WKS | F | F |
| 45 | 24 | 18 WKS | F | F |
| 46 | 31 | 21 WKS | F | F |
| 47 | 33 | 20 WKS | F | F |
| 48 | 23 | 20 WKS | F | F |
| 49 | 19 | 19 WKS | F | F |
| 50 | 28 | 21 WKS | M | M |
| 51 | 23 | 17 WKS | M | M |
| 52 PREGNANCY MISCARRIED | 20 | 16 WKS | F | |
| 53 | 22 | 18 WKS | F | F |
| 54 | 28 | 18 WKS | M | M |
| 55 | 22 | 19 WKS | F | F |
| 56 | 21 | 20 WKS | F | F |
| 57 | 26 | 21 WKS | F | F |
| 58 | 24 | 16 WKS | F | F |
| 59 | 17 | 18 WKS | F | F |
| 60 | 19 | 17 WKS | F | F |
| 61 | 28 | 19 WKS | M | M |
| 62 | 23 | 17 WKS | M | M |
| 63 | 22 | 19 WKS | M | M |
| 64 | 21 | 19 WKS | F | F |
| 65 TWINS | 24 | 22 WKS | F | F |
| 66 | 35 | 18 WKS | F | F |
| 67 | 31 | 19 WKS | F | F |
| 68 | 39 | 17 WKS | F | F |

TABLE 1-continued

| Sample Number | Mother's Age (Years) | Gestational Age at Testing (Weeks) | Test Result | Confirmed Result |
|---|---|---|---|---|
| 69 | 43 | 17 WKS | M | M |
| 70 | 17 | 21 WKS | M | M |
| 71 | 18 | 22 WKS | F | F |
| 72 NOT SUPERVISED TEST | 19 | 16 WKS | M | F |
| 73 | 23 | 18 WKS | F | F |
| 74 | 26 | 17 WKS | F | F |
| 75 | 25 | 16 WKS | M | M |
| 76 | 21 | 18.5 WKS | F | F |
| 77 | 17 | 20 WKS | M | M |
| 78 | 23 | 21 WKS | M | M |
| 79 | 19 | 24 WKS | F | F |
| 80 | 27 | 22 WKS | M | M |
| 81 | 22 | 19 WKS | F | F |
| 82 | 27 | 19 WKS | F | F |
| 83 | 33 | 17 WKS | F | F |
| 84 | 29 | 18 WKS | F | F |
| 85 | 20 | 18 WKS | F | F |
| 86 | 20 | 19 WKS | F | F |
| 87 | 24 | 19 WKS | M | M |
| 88 | 19 | 21 WKS | M | M |
| 89 | 18 | 22 WKS | F | F |
| 90 | 38 | 20 WKS | F | F |
| 91 | UNKNOWN | 22 WKS | F | F |
| 92 | 24 | 21 WKS | M | M |
| 93 | 19 | 22 WKS | F | F |
| 94 | 22 | 19 WKS | F | F |
| 95 | 26 | 17 WKS | M | M |

TABLE 2

| Species | Mother's Age (Years) | Gestational Age at Testing (Weeks) | Test Result | Confirmed Result |
|---|---|---|---|---|
| Equine | 8 | 20 | M | M |
| Bovine 1 | 17 | 18 | F | F |
| Bovine 2 | 9 | 22 | F | F |

As noted above, water absorption in basic salts can cause the undesirable mixing and reaction of the transition metals components of the first layer and basic salts of the second layer. As part of the present disclosure, it was recognized that the presence of water facilitates a chemical reaction between the above-described transition metals and basic salts can which, in turn, can significantly decrease the shelf life of a gender test kit containing these components. It was further discovered that transition metals and basic salts in an atmosphere that is substantially free of water can substantially decrease the rate of reaction between the transition metals and basic salts, thereby greatly extending the shelf-life of the kit. In some cases the atmosphere substantially free of water can eliminate the need to separate the transition metals and basic salts from each other with the neutral filler, thereby substantially the kit's manufacturing process.

Figure 9:
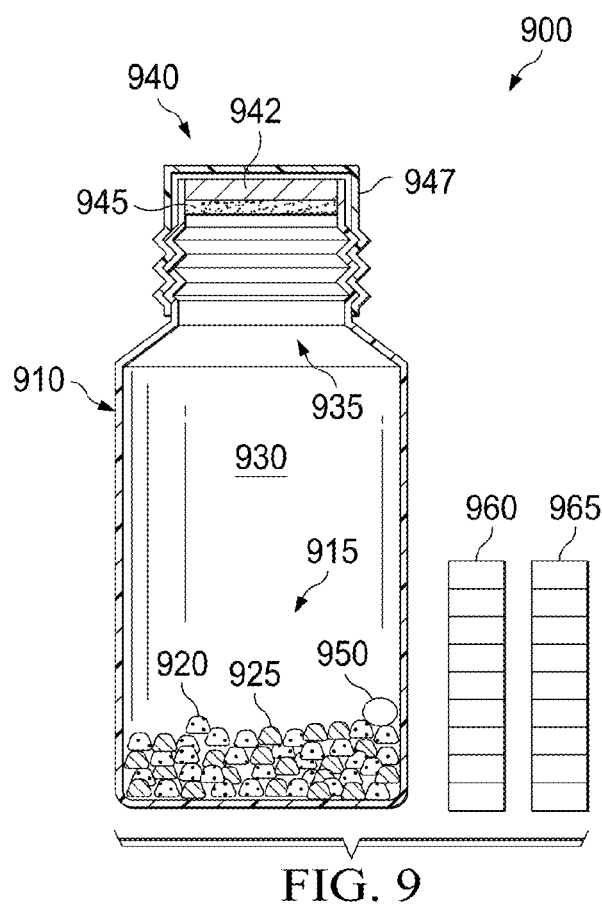
FIG. 9 illustrates a cross-sectional view of an example gender test kit of the present invention.

Another embodiment of the invention is a kit for determining the gender of an unborn fetus. FIG. 9 illustrates a cross-sectional view of an example gender test kit 900 of the present invention. The kit 900 comprises a container 910 having a solid composition 915 therein. The solid composition 915 including a basic salt 920 and a transition metal 925. An atmosphere 930 in the container 910 is substantially free of water. For the purposes of the present invention, the substantially term free of water as used herein means that the atmosphere 930 has about 10 percent or less than the maximum concentration of water vapor that can be attained in the atmosphere 930 for a given pressure and temperature of the atmosphere 930.

In some embodiments the atmosphere 930 is composed of dry nitrogen (e.g., about 100 percent N2 gas with than about 1 percent H2O by weight) or dry air. In other embodiments, the atmosphere 930 is composed of dry air (e.g., about 100 percent air with less than about 1 percent H2O by weight). In still other cases, the atmosphere 930 is composed of an inert gas (e.g., about 100 percent argon or xenon less than about 1 percent $H_2O$ by weight). Based on the present disclosure one skilled in the art would appreciate that the atmosphere 930 could be composed of other dry (e.g., water free) gases.

It is preferable for the container to 910 to be air-tight so that water vapor can not diffuse into the container 910. For instance, the container 910 can be composed of a material that is resistant to the diffusion of air through it, such as glass, polycarbonate or polystyrene. It is also desirable for an opening 935 of the container 910 to be covered with an air-tight seal 940. For instance, in some embodiments, the container 910 (e.g., a bottle or tube) is covered with a metal foil seal 940 that is adhesively coupled to the opening 935 (e.g., a screw top opening). In some embodiments, the metal foil seal 940 includes a metal layer 942 (e.g., aluminum foil) and adhesive backing layer 945 (e.g., a heat activated adhesive). In some cases the air-tight seal 940 can include a cap 947 (e.g., a plastic screw-top cap)

In some cases, such as shown in FIG. 9, the basic salt 920 and transition metal 925 of the composition 915 are intermixed with each other. E.g., the basic salt 920 and transition metal 925 can be solid particles that are homogenously mixed with each other. Having the basic salt 920 and transition metal 925 are intermixed with each other can facilitate the rapid generation of heat and dissolving of the particles when a urine sample is added to the contain 930.

In other cases, however, it may be desirable for the basic salt 920 and transition metal 925 of the composition 915 to be formed as separate layers in the contain 910 (e.g., first and second layers 110, 120 FIG. 1). Providing the basic salt 920 and transition metal 925 as separate layers decreases the contact between the individual particles of basic salt 920 and transition metal 925. This, in turn, can slow down their rate of reaction and thereby increase the shelf-life of the kit 900 in cases where there is still some water vapor in the atmosphere 930, or water vapor slowly diffuses into the container 910.

In still other cases, it is desirable to for the separate layers of basic salt 920 and a transition metal 925 to be separated by a third layer of neutral filler (e.g., layer 130, FIG. 1) in the containing 910. The presence of the neutral filler layer can further can slow down the rate of reaction between the basic salt 920 and transition metal 925 and thereby further increase the shelf-life of the kit 900.

Any of the embodiments of basic salt, transition metal and neutral described herein can be used in the kit 900. The kit 900 can include additional components to facilitate its effectiveness for gender testing. For instance, the solid composition 915 can further includes an indicator 950 configured to enhance a color change in a solution resulting from mixing the solid composition 915 with testosterone-containing urine. For instance, the kit 900 can further include indicator strips 960, 965 that can each have a colored surface that matches a color of one of either a solution resulting from mixing the solid composition 915 with urine from a female that is pregnant with either a male fetus, or, a female fetus.

Another embodiment of the invention is a method of manufacture a kit for determining the gender of an unborn fetus.

Figure 10:
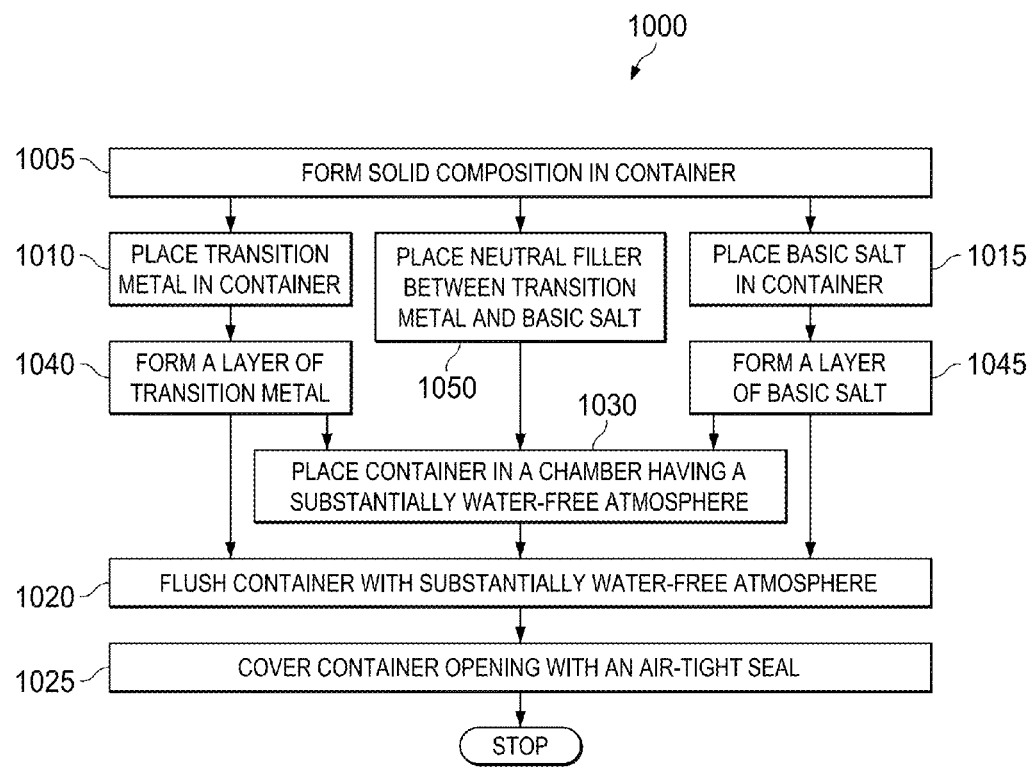
FIG. 10 presents a flow diagram of a method of manufacturing a gender test kit, such as the gender test kit of FIG. 9.

FIG. 10 presents a flow diagram of a method 1000 of manufacturing a gender test kit, such as the gender test kit 900 of FIG. 9.

With continuing reference to FIGS. 9 and 10, the method 1000 comprises a step 1005 of forming a solid composition 915 in a container 910. Forming the composition 915 includes a step 1010 of placing a transition metal 925 in the container 910, and, a step 1015 of placing a basic salt 920 in the container 910. The method 1000 also comprises a step 1020 of flushing the container 910 with an atmosphere 930 that is substantially free of water.

In some embodiments the flushing in step 1020 is performed for at least about 1 minute. For example, a dry nitrogen or dry air atmosphere 930 can be flushed via a tube inserted into the container 910. In other cases, such as when the when components of the solid composition 915 (e.g., basic salt 920 or transition metal 925) contain water, a longer flushing time (e.g., 5 minutes or greater) can be desirable to drive water out of the solid composition 915.

The method 1000 can further include a step 1025 covering an opening in said container with an air-tight seal 940. The term air-tight seal as used herein means that the atmosphere 930 in the sealed container does not substantially increase in water content (e.g., less than 10 percent increase) for a storage time at room temperature of at least about 1 month and more preferable at least about 6 months and even more preferably at least about 1 year. In some cases, it is desirable to cover the container 910 in step 1020 as soon as possible after flushing in step 1020 so as to minimum the amount of water vapor re-entering the container 910. For example, in some cases, the covering in step 1025 is done within about 10 seconds of ending the flushing step 1020.

In other cases, the flushing and covering steps 1020, 1025 can both be performed in step 1030 with the entire container 910 placed in a chamber that contains the atmosphere 930. This can obviate the need to rapidly cover the container in step 1025 soon after flushing the container in step 1020.

Any of the solid compositions and their methods of preparation described herein can be used as part of forming the solid composition 915 of the kit 900. For instance, forming the solid composition 915 in step 1005 can include a step 1040 forming a layer (e.g., layer 110, FIG. 1) of the transition metal, and step 1045 of forming a layer (e.g., layer 120, FIG. 1) of the basic salt, wherein the transition metal layer 110 and basic salt layer 120 are separate layers. For instance, wherein forming the solid composition 915 in step 1005 can further include a step 1050 of placing a neutral filler in the container 930 (e.g., a layer 130, FIG. 1), wherein the neutral filler separates the transition metal layer 110 and said basic salt layer 120.

Figure 11:
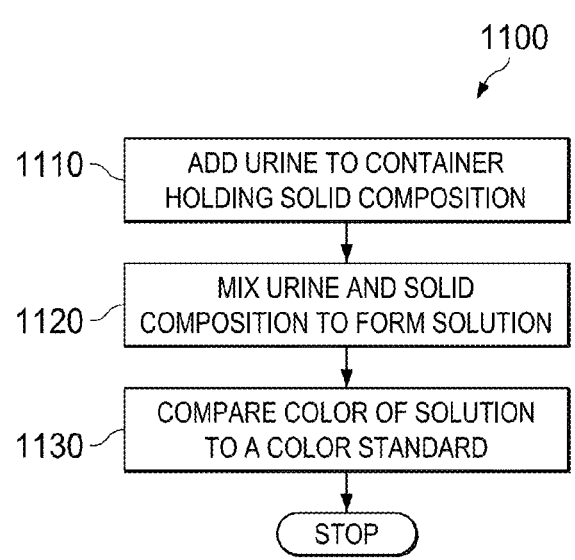
FIG. 11 presents a flow diagram of method of determining the gender of an unborn fetus, such as performed using the gender test kit of FIG. 9.

Still another embodiment of the invention is a method of determining the gender of an unborn fetus. FIG. 11 presents a flow diagram of a method 1100 of determining the gender of an unborn fetus, such as performed using the gender test kit 900 of FIG. 9.

The method 1100 comprises a step 1110 of adding urine from a pregnant female to a container 910 holding the above-described solid composition 915 and atmosphere 930 substantially free of water. The method 1100 also comprises a step 1120 of mixing the solid composition 915 and the urine to form a solution. The method 1100 further comprises a step 1130 of comparing a color of the solution to a color standard (e.g., the indicator strips 960, 965 of the kit 900) to determine a gender of an unborn fetus carried by the female.

Based on the present disclosure, one skilled in the art would appreciate how other steps such as described in the context of FIG. 7 could be incorporated into the method 1100.

Although the present invention has been described in detail, those skilled in the art should understand that they can make various changes, substitutions and alterations herein without departing from the scope of the invention in its broadest form.

What is claimed is:

1. A kit for determining the gender of an unborn fetus, comprising:
 a container holding a solid composition therein, said solid composition including a basic salt and a transition metal separated by a neutral filler, wherein an atmosphere in said container is substantially free of water.

2. The kit of claim 1, wherein said atmosphere is composed of dry nitrogen or dry air.

3. The kit of claim 1, wherein an opening of said container is covered with an air-tight seal.

4. The kit of claim 1, wherein an opening of said container is covered with a metal foil seal that is adhesively coupled to said opening.

5. The kit of claim 1, wherein said basic salt and a transition metal form separate layers in said container.

6. The kit of claim 1, wherein said basic salt and a transition metal form separate layers in said container and a third layer of a neutral filler separating said layer of said basic salt from said layer of said transition metal.

7. The kit of claim 1, wherein said basic salt comprises a water-soluble alkali metal hydroxide.

8. The kit of claim 1, wherein said transition metal includes aluminum.

9. The kit of claim 1, wherein said neutral filler includes a neutral salt.

10. The kit of claim 1, wherein said neutral filler comprises a water-soluble polymer.

11. The kit of claim 1, wherein said solid composition further includes an indicator configured to enhance a color change in a solution resulting from mixing said solid composition with testosterone-containing urine.

12. The kit of claim 1, further including indicator strips that each have a colored surface that matches a color of one of either a solution resulting from mixing said solid composition with urine from a female that is pregnant with a male fetus, or, a female fetus.

13. A method for manufacturing a kit for determining the gender of an unborn fetus, comprising:
 forming a solid composition in a container, including:
 placing a transition metal in a container;
 placing a basic salt in said container;
 separating the transition metal and the basic salt with a neutral filler; and
 flushing said container with an atmosphere that is substantially free of water.

14. The method of claim 13, wherein said flushing is performed for at least about 1 minute.

15. The method of claim 13, further including covering an opening in said container with an air-tight seal.

16. The method of claim 15, wherein forming said air-tight seal includes covering said opening within about 10 seconds of ending said flushing.

17. The method of claim 13, wherein said atmosphere is composed of dry nitrogen or dry air.

18. The method of claim 13, wherein forming said solid composition includes forming a layer of said transition metal, and forming a layer of said basic salt, wherein said transition metal layer and said basic salt layer are separate layers.

19. The method of claim 13, wherein forming said solid composition further includes placing a neutral filler in said container, wherein said neutral filler separates said transition metal layer and said basic salt layer.

20. A method determining the gender of an unborn fetus, comprising:
  adding urine from a pregnant female to a container holding a solid composition, said solid composition including a basic salt and a transition metal separated by a neutral filler, wherein an atmosphere in said container is substantially free of water;
  mixing said solid composition and said urine to form a solution; and
  comparing a color of said solution to a color standard to determine a gender of an unborn fetus carried by said female.

* * * * *